United States Patent [19]

Horzinek et al.

[11] 4,293,653

[45] Oct. 6, 1981

[54] METHOD FOR PROPAGATING FELINE INFECTIOUS PERITONITIS VIRUS

[76] Inventors: Marian C. Horzinek, Kramsvogellaan 128, Bilthoven; Albertus D. M. E. Osterhaus, Dr. Breveestraat 16, Bunnik, both of Netherlands

[21] Appl. No.: 29,591

[22] Filed: Apr. 12, 1979

[51] Int. Cl.³ .............................................. C12N 7/08
[52] U.S. Cl. .................................................... 435/237
[58] Field of Search ................... 195/1.3, 1.8; 435/237

[56] References Cited

PUBLICATIONS

Zbl. Vet. Med. B. 25, 806–815, (1978); 816–825, (1978); 301–307, (1978).

Primary Examiner—Frederick E. Waddell
Attorney, Agent, or Firm—Stevens, Davis, Miller & Mosher

[57] ABSTRACT

A process for propagating feline infectious peritonitis (FIP) virus in which suckling rodents are intracerebrally inoculated with infectious cat material, containing the feline infectious peritonitis virus, the virus is replicated in the brain of the infected suckling rodent and the infected brain material is then harvested from the infected rodents.

5 Claims, 1 Drawing Figure

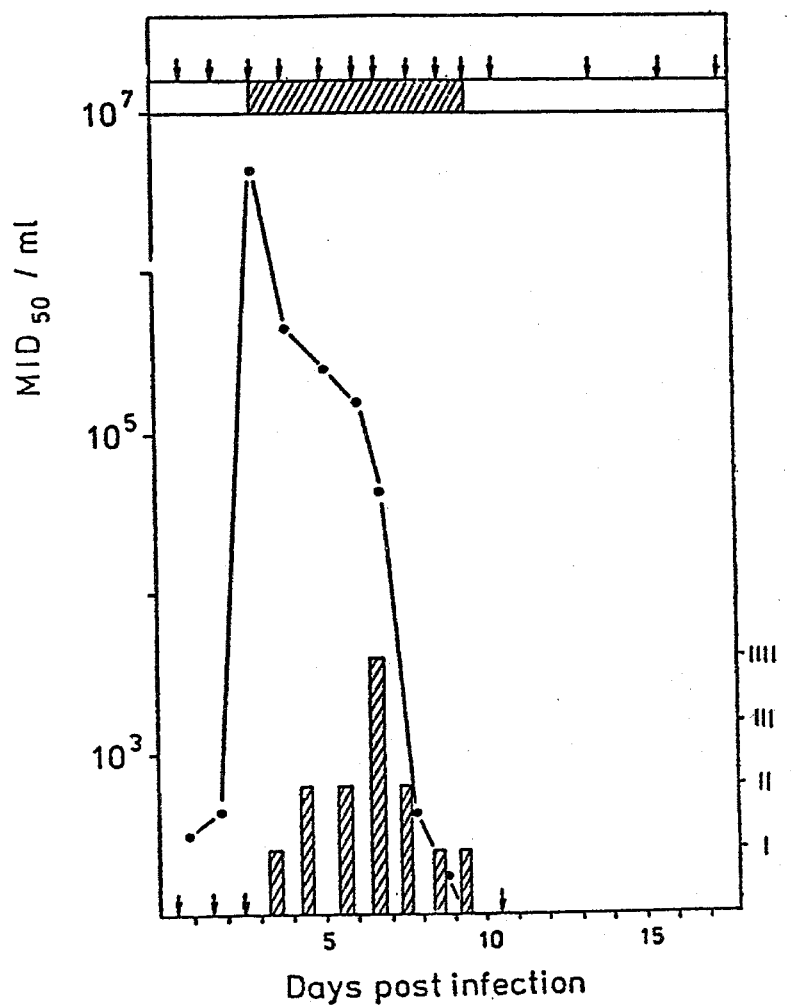
Figure I

METHOD FOR PROPAGATING FELINE INFECTIOUS PERITONITIS VIRUS

The present invention relates to a new method for propagating feline infectious peritonitis (FIP) virus and to so obtained virus strains.

FIP is one of the most important diseases affecting domestic and wild Felidae. The clinical symptoms of naturally occuring FIP are not very characteristic at the beginning of the disease. The affected animal shows anorexia, anemia, usually an elevated temperature curve and general depression. In classical cases these symptons are accompanied by a gradual abdominal distension which in conbination with progressive emaciation often results in a dehydrated animal with an enlarged undulating abdomen. Once these symptoms have become evident, the animal succumbs within one to eight weeks. So the diagnosis of FIP is not difficult in classical cases, where extensive accumulations of the characteristic exudate are demonstrated in the abdominal cavity. However, with less or no exudate present, diagnosis constitutes a greater challenge. The clinical symptoms in combination with laboratory tests may result in cumulative evidence.

So far therapeutic measures have rarely been found effective and the prognosis of the disease must be considered very poor, once the clinical symptoms have developed. Also no prophylactic measures for FIP are available at this moment, where pathogenesis and mode of transmission are still open questions.

FIP virus was shown to possess many of the physical properties of Coronaviridae family members and support for this classification has been obtained recently from neutralization an immunofluoresence studies showing an antigenic relationship between FIP virus and the coronavirus causing transmissible gastroenteritis (TGE) of swine. Most coronaviruses so far described are very difficult to isolate in cell culture.

Notwithstanding strenuous efforts by many investigators numerous attempts to propagate FIP virus in chicken-embryos, primay feline cells and continuous cell lines have failed.

So far in vitro virus growth could be demonstrated only in cultures of cells derived from the peritoneal exudates of kittens after experimental infection with FIP virus (Am. J. Vet. Res. 37 (1976), 567–572), and recently replication of FIP virus in organ cultures of small intestine of one to nine week old specific pathogen free (SPF) kittens has been described (Cornell Vet., 68 (3), (1978), 411–417).

It has now been found that FIP virus can be succesfully propagated in the brain of suckling rodents, preferably mice, rats and hamsters.

Therefore, it is an object of the invention to provide a new method for propagating FIP virus and to provide FIP virus strains obtained by this method.

The invention relates to a process for propagating FIp virus by inoculating suckling rodents intracerebrally (i.c.) with infectious cat material (starting material) or with a brain homogenate of i.c. infected rodents (passage material), and harvesting the virus containing brain material.

The invention further relates to FIP virus containing brain material obtained according to the method of the invention, and to the FIP virus strains obtained by purification of such brain material.

The invention will be described in more detail by means of the following experiments.

EXPERIMENT A

SPF-mice were kept in a laminar flow hood. Litters containing 7 to 14 animals not older than 24 hours were i.c. infected with 5 $\mu$l per animal of a 10% (w/v) cat liver suspension (starting material) or of a 40% mouse brain homogenate (passage material), using a Hamilton syringe. As starting material the third cat passage of the Dahlberg strain of FIP virus (vide Zbl. Vet. Med. B 24 (1977), 398–405) was used as a 10% (w/v) homogenate of infectious liver tissue in phosphate buffered saline (PBS). A control passage series was done using a normal cat liver homogenate as starting material. The animals were examined daily for clinical signs. After 7 days the mice were decapitated, the brains were removed and divided into two portions each, one serving for demonstrating viral antigen using the direct immunofluorescence test (IFT), the other (after pooling ahd homogenizing) for further passaging.

Direct IFT was done as follows. From the ascitic fluid of a FIP-field case $\gamma$-globulin was prepared by repeated precipitation (3 times) with ammonium sulphate at 50% saturation. The preparation was labelled with FITC using standard techniques (P. K. Vogt, Fundamental techniques in Virology, 1969, edited by K. Habel and N. P. Salzman, Acad. Press New York, pages 316–326). Cryostat sections from mouse brains and cat organs were acetonefixed (10 minutes at $-20°$ C.), dried, washed with PBS and with distilled water, and dried again. A working dilution of the obtained conjugate in PBS was applied to the sections and the preparations were incubated for 30 minutes at 37° C. in a moist chamber. After 3 rinses in PBS and one in distilled water the slides were dried and mounted in Uvak (Seatle, High Wycombe Bucks. England).

Three litters on one day old mice were inoculated i.c. with infectious cat liver material and one litter with normal cat liver material. Passages were performed at weekly intervals by inoculating i.c. one day old litters of mice with a 40% homogenate of mouse brain suspension as mentioned above. No clinical signs were observed in the experimental animals during the short period of observation. The results of direct IFT applied to brain sections of different passage levels are shown in Table I:

TABLE I

| Passage history of FIP virus (strain Dahlberg) in suckling mouse brain | | | | | | | | | |
|---|---|---|---|---|---|---|---|---|---|
| Passage number | 1 | 2 | 3 | 4 | 5 | 6 | 7 | 8 | 9 |
| Isolation | | | | | | | | | |
| A | $-^1$ | $+^2$ | + | + | 10/10$^3$ | 10/10 | 8/8 | 10/10 | 10/10 |
| B | — | — | — | — | | | | | |
| C | — | — | — | — | | | | | |
| D(control) | — | — | — | — | | | | | |
| Reisolaton | | | | | | | | | |
| E | — | — | 4/10 | 10/10 | 10/10 | | | | |
| F | — | — | 9/9 | 8/8 | 10/10 | | | | |

TABLE I-continued

| Passage history of FIP virus (strain Dahlberg) in suckling mouse brain | | | | | | | | | |
|---|---|---|---|---|---|---|---|---|---|
| Passage number | 1 | 2 | 3 | 4 | 5 | 6 | 7 | 8 | 9 |
| G | — | — | — | — | — | | | | |
| H | — | — | — | — | — | | | | |
| I(control) | — | — | — | — | — | | | | |

[1] no fluorescence observed
[2] fluorescence observed in ≧1 brain section
[3] numerator: number of IFT-positive mice
denominator: number of inoculated mice Using the labelled anti FIP γ-globulin, clear-cut fluorescence was observed in one of the three FIP virus infected mouse series (A in table I), from the second passage onward. The two other FIP series and the control series remained negative through four subsequent passages.

To confirm the results of this propagation experiment reisolation was attempted from the same cat liver material (starting material). Virus multiplication was detected in two of the four passage series (E and F in table I) from the third passage on.

In order to determine the specificity of the observed fluorescence for FIP virus in mouse brain a group of three SPF kittens which had been shown seronegative for TGE virus (Zbl. Vet. Med. B, 24, (1977), 835–841) were used. Two of the animals were inoculated with fluorescence positive material of the 6th mouse passage (isolation series A of table I) by injection of 1.0 ml quantities of a clarified (centrifugation 2.5 minutes at $10,000 \times g$) 40% (w/v) mouse brain homogenate via the intraperitoneal route. The third kitten served as a contact control. The animals were checked daily for rise in body temperature and overt clinical signs. One inoculated cat showed a distinct rise in body temperature on day 13 post infection (p.i.) and gradually developed classical FIP symptoms; death occurred on day 20 p.i.

EXPERIMENT B

Nine one day old conventionally reared rats wer inoculated i.c. with 25 μl 50% (w/v) suspension of brain material from the 10th or 11th suckling mouse brain (SMBr) passage of FIP virus obtained according to experiment A. Two of them died on the 6th day p.i. and a third animal was missing. One animal served as a mock-infected control. Seven days p.i. the brains of all rats were tested in the direct IFT. Distinct fluorescence, comparable to that found in the FIP virus infected suckling mouse brain, was found in the brain preparations of the eight infected animals (first SRBr passage). The brain of the mock-infected control rat was negative in this test.

A second SRBr passage showed essentially the same results. All 4 infected animals (25 μl i.c.) showed a positive IFT. For specificity reasons the passage procedure was repeated in 6 one day old SPF rats: all five surviving animals, showed IFT positive brain preparations.

EXPERIMENT C

The same passage procedures as in experiment B were performed in conventionally reared one day old hamsters. The eight infected animals (25 μl i.c. of a 50% (w/v) suspension of the 10th or 11th SMBr passage of FIP virus) of the first passage and the five animals in a subsequent passage showed immunofluorescence in their brains on the 7th day p.i.

EXPERIMENT D

This experiment was performed to investigate the influence of the age of the infected animal. Litters of 8 to 12 mice were injected i.c. with about 100 $MID_{50}$ of material of the 6th mouse brain passage at an age of 2, 4, 6, 8 and 10 days respectively. Immunofluorescence as evidenced by the brain smear technique was determined on day 7 p.i.

As can be seen from Table II, mice can be infected regularly up to 4 days of age. In older animals fluorescence was seen with decreasing frequency and intensity.

TABLE II

Age susceptibility of baby mice for FIP virus (6th mouse brain passage), after injection of about 100 $MID_{50}$ units via the intracerebral route into litters of 8 to 12 animals.

| Animal age (days) | Results of IFT |
|---|---|
| 2 | positive |
| 4 | positive |
| 6 | negative |
| 8 | positive |
| 10 | negative |

EXPERIMENT E

The extent of FIP virus multiplication in i.c. inoculated one day old mice was studied by examining cryostat sections through several organs at 7 days p.i. As can be seen from Table III only cells of the central nervous system and the eye were found positive by IFT.

TABLE III

Ogran immunofluorescence in one day old baby mice inoculated with FIP virus (11th mouse brain passage) via the intracerebral route.

| organ | animal no. | | | | | | | | | |
|---|---|---|---|---|---|---|---|---|---|---|
| | 1 | 2 | 3 | 4 | 5 | 6 | 7 | 8 | 9 | 10 |
| brain | + | + | + | + | + | + | ± | + | + | + |
| spinal cord | + | + | + | + | + | φ | ± | + | + | + |
| eye | ND | ND | ND | + | + | ND | ± | ND | + | + |
| heart | φ | φ | φ | φ | φ | φ | φ | φ | φ | φ |
| lung | φ | φ | ND | ND | ND | φ | φ | φ | φ | φ |
| liver | φ | φ | ND | φ | φ | φ | φ | φ | φ | φ |
| spleen | ND | ND | φ | φ | φ | φ | φ | φ | φ | φ |
| kidney | φ | φ | φ | φ | φ | φ | φ | φ | φ | φ |
| pancreas | φ | φ | ND | φ | φ | φ | φ | φ | φ | φ |

ND = not done
+ = distinct fluorescence
± = few fluorescence cells
φ = no fluorescence

EXPERIMENT F

With the aim of studying the time course of appearance and disappearance of fluorescent antigen in brain cells, one day old mice were infected by i.c. injection of FIP virus material (10th SMBr passage) and examined at daily intervals. The amount of fluorescent cells in freshly prepared smears was scored as arbitrary units. In three experiments no antigen was found during the first three days, earliest distinct fluorescence being detectable at 72, 88 and 96 hours after infection respectively. On the other hand fluorescence was absent in mice sacrificed later than 12 days after infection (246, 248 and 288 hours p.i.) The number of fluorescent cells reached a maximum about 7 days p.i. as shown in FIG. I.

EXPERIMENT G

The growth curve of FIP virus in suckling mouse brain was determined by investigating multiplication of FIP virus in litters of one day old mice.

Multiplication of FIP virus led to more than $10^4$ fold increase of infectivity between the 2nd and 3rd day after intracerebral inoculation. A subsequent rapid decline from maximum titers exceeding $10^6 ID_{50}$ units/ml to undetectable levels occured between days 3 to 10 p.i. In FIG. I both the course of appearance and disappearance of fluorescent antigen (experiment F) and the growth curve of FIP virus are shown. A rapid decrease of infectivity (indicated with points) after day 3 p.i. is seen. At the days indicated by arrows, immunofluorescence tests were performed on brain smears of infected mice in two independent experiments. The presence of viral antigen is indicated by the hatched areas, its quantity was estimated and given in arbitrary units (right ordinate of FIG. I).

It can be seen in FIG. I that the maxima of infectivity (3 days p.i.) and of immunofluorescence intensity (7 days p.i.) do not coincide.

It appears from the above described experiments A to G that FIP virus multiplication occurs in the brain of suckling rodent such as mice, rats and hamsters.

Highest susceptibility for infection with FIP virus after i.c. inoculation was observed in mice between 1 and 4 days of age. Distinct immunofluorescence was found between 4 and 10 days postinfection, with a maximum at 7 days p.i.

The growth curve of FIP virus in neonatal mice showed a maximum of infectivity at 3 days p.i.

It will be clear for a person skilled in the art that the present invention provides a practically applicable possibility to obtain FIP virus strains in sufficient quantities by using easy available and cheap small laboratory animals.

It is particularly emphasized that the contents of:
(1) Zbl. Vet. Med. B, 25 (1978), 301–307;
(2) Zbl. Vet. Med. B, 25 (1978), 806–815 and
(3) Zbl. Vet. Med. B, 25 (1978), 816–825
is incorporated by reference herein.

We claim:

1. A process for propagating feline infectious peritonitis virus which comprises the steps of:
   (a) inoculating suckling rodents intracerebrally with infectious cat material;
   (b) replicating the virus in the brain of said inoculated rodents;
   (c) harvesting FIP virus containing brain material from said inoculated rodents; and
   (d) optionally inoculating rodents, with the so obtained virus containing brain material for further passages.

2. The process of claim 1 wherein said rodents are inoculated intracerebrally at 1 to 4 days of age.

3. The process of claim 1 wherein said infectious cat material is a homogenate of infectious liver tissue in phosphate buffered saline.

4. The process of claim 1 wherein the virus containing brain material is harvested at 2 to 10 days post inoculation.

5. Brain material obtained according to the process of claim 1.

* * * * *